United States Patent [19]

Hara et al.

[11] Patent Number: 4,613,447
[45] Date of Patent: Sep. 23, 1986

[54] COMPOSITION FOR CLEANSING AND WIPING THE CIRCUMANAL REGION

[75] Inventors: Kenji Hara, Ichikaimachi; Yasuteru Eguchi, Utsunomiya, both of Japan

[73] Assignee: KAO Corporation, Tokyo, Japan

[21] Appl. No.: 615,759

[22] Filed: May 31, 1984

[30] Foreign Application Priority Data

Jun. 7, 1983 [JP] Japan ................. 58-101336

[51] Int. Cl.$^4$ ............................................. C11D 17/00
[52] U.S. Cl. ................................. 252/91; 252/89.1; 252/174.15
[58] Field of Search ............ 252/174.15, 91, 89.1; 106/8, 9; 15/209 C, 229 R

[56] References Cited

U.S. PATENT DOCUMENTS

| | | | |
|---|---|---|---|
| 3,072,952 | 1/1963 | Cox | 15/209 C |
| 3,177,055 | 4/1965 | Ruckle et al. | 15/209 C |
| 3,284,963 | 11/1966 | Lanham et al. | 15/209 C |
| 4,370,319 | 1/1983 | Chapin et al. | 424/184 |
| 4,382,960 | 5/1983 | Flom | 514/77 |

FOREIGN PATENT DOCUMENTS

| | | |
|---|---|---|
| 0007120 | 1/1980 | European Pat. Off. |
| 0037011 | 10/1981 | European Pat. Off. |
| 714795 | 9/1954 | United Kingdom |
| 803545 | 10/1958 | United Kingdom |
| 803289 | 10/1958 | United Kingdom |
| 945061 | 12/1963 | United Kingdom |
| 965236 | 7/1964 | United Kingdom |
| 1277324 | 6/1972 | United Kingdom |
| 1376649 | 12/1974 | United Kingdom |
| 1604853 | 12/1981 | United Kingdom |

OTHER PUBLICATIONS

Derwent Abstract, Accession No. 82-55615E/27, Japanese Pat. No. J57002215-A, Jan. 7, 1982.
Derwent Abstract, Accession No. 48071Y/27, Japanese Pat. No. J5 2064-415, Jul. 27, 1977.
Seifen-Ole-Fette-Wachse, vol. 108, No. 14, Sep. 1982, Augsburg, (Germany) p. 428, column on the left, under "Moderne Silicongele".
Chem. Abst., vol. 79, 1973, pp. 316-317, abstract No. 96850g, Columbus, Ohio, US; & JP-A-73 33 039 (Nippon Chemical Co., Ltd.) May 7, 1973.

*Primary Examiner*—Amelia B. Yarbrough
*Attorney, Agent, or Firm*—Oblon, Fisher, Spivak, McClelland & Maier

[57] ABSTRACT

A composition of cleansing and wiping skin in the circumanal region which comprises at least one oil selected from the group consisting of vegetable oils, animal oils and synthetic oils, and a silicone oil and has a viscosity of not more than 30 cs as measured at 5°0 C.

The composition according to the invention is preferably used after excrement is wiped off with usual toilet paper and facilitates removal of excrement residues on the skin of circumanal region. Besides, when the composition is applied to the circumanal skin prior to defecation, it prevents excrement from sticking to the skin or makes excrement easy to be wiped off.

The composition may be sprayed on conventional toilet paper or impregnated into nonwoven fabric, cloth, paper etc. on application.

Such materials containing the composition according to the invention is effective in preventing any aggravation to hemorrhoids or the like.

6 Claims, 2 Drawing Figures

COMPOSITION FOR CLEANSING AND WIPING THE CIRCUMANAL REGION

BACKGROUND OF THE INVENTION (i) Field of the Invention

This invention relates to a composition for cleansing and wiping the circumanal region which makes it easy to remove that portion of excrement residues which remains in the circumanal region after wiping off the excrement with a conventional toilet paper or the like following defecation and which, when applied to the skin in the circumanal region prior to defecation, makes it difficult for the excrement to stick to the skin during the subsequent defecation or makes it easy to wipe off the excrement from the skin and thereby keeps the circumanal region clean and prevents aggravation of symptoms found in the circumanal region, such as hemorrhoids, eruption and itching.

(ii) Description of the Prior Art

For the wiping and cleansing treatment of the anus following defecation, toilet paper is generally used. Bidets and other washing apparatus using warm water, and cleansing cotton are also used, but rarely. From the viewpoint of skin irritation or filth removal, washing with warm water is the most desirable. However, washing apparatus using warm water are expensive and require cumbersome handling, and therefore have not come into wide use yet. Cleansing cotton each time costs much, feels cold and is disadvantageous in that it cannot be disposed in a flush toilet. For these reasons, the actual situation is that toilet paper and coarse toilet paper are most generally used in wiping the anus after defecation.

The skin in the circumanal region has small wrinkles and creases and hair, and those portions of excrement residues which have got into such minute parts can be wiped off only with difficulty. Furthermore, sticking excrement residues, after solidification, are difficult to remove.

On the other hand, regeneration products account for about 70% of toilet paper and coarse toilet paper which are generally used. Physically, they are rather tough and therefore crumpled soft prior to use, but even they may injure the skin, causing excoriation. Excrement residues sticking to the skin parovide sources of propagation of bacteria, and decomposition products and the like produced by bacteria promote aggravation of the injured skin or cause itching, eruption or sore of the circumanal region. To clean the circumanal region is very important also to general public from the public health standpoint. In particular, to babies having a delicate skin and bedridden old people or to those suffering from diseases of the anus, such as hemorrhoids, that is important. Such people having some or other skin lesions in the circumanal region are sensitive to stimuli to the skin in the circumanal region and easily feel a pain upon stimulation in said region. Consequently, they tend to reduce the wiping force, and the results are insufficient wiping and increase in excrement residues.

Some of those with hemorrhoids, for instance those with internal hemorrhoids or anal prolapse, must force the internal hemorrhoids or rectal part, which had come out of the anus, back into the anus after defecation so that pains due to friction between the underwear and affected part can be removed. In this case, they cannot but manage to effect the insertion with fingers while bearing the pain. A device which physically makes the insertion easy is desired.

SUMMARY OF THE INVENTION

Under these circumstances, the present inventors conducted intensive study so as to develop a composition for cleansing and wiping the circumanal region which might be used after defecation in a simple and easy manner, might remove, to a sufficient extent, excrement residues remaining after wiping with toilet paper, might keep the circumanal region clean and might prevent aggravation of various symptoms of the circumanal region, such as hemorrhoids, eruption and itching. As a result, they found that the above object can be accomplished by using a composition which comprises an oil and a silicone oil and has a specific viscosity. This finding has led to completion of the present invention.

Thus, the invention provides a composition of cleansing and wiping the circumanal region which comprises at least one oil selected from the group consisting of vegetable oils, animal oils and synthetic oils, and a silicone oil and has a viscosity of not more than 30 cs as measured at 5° C.

DETAILED DESCRIPTION OF THE INVENTION AND PREFERRED EMBODIMENTS

Figure 1:
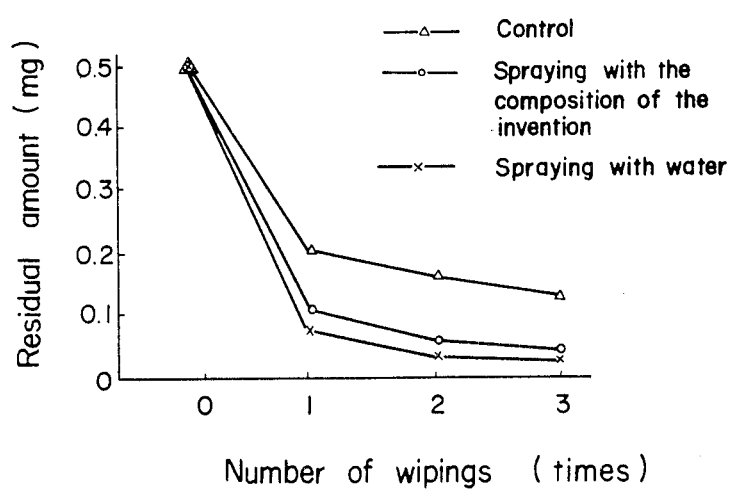
FIG. 1 is a graphic representation of the change in residual feces amount in the circumanal region with the number of wipings.

The vegetable oils, animal oils and synthetic oils to be used in the practice of the invention include such vegetable oils as olive oil, almond oil, jojoba oil, peanut oil, castor oil, coconut oil, palm oil, sunflower oil, cottonseed oil, hardened coconut oil and hardened palm oil, such animal oils as lanolin, turtle oil, beeswax, squalene, squalane and pristane, and such synthetic oils as liquid paraffin and fatty acid triglycerides (e.g. glycerol tri-2-ethylhexanoate). Among them especially preferred are jojoba oil, squalane and glycerol tri-2-ethylhexanoate.

Among the above oils, liquid paraffin, olive oil and lanolin have been used generally in preparing baby oils and oils for cosmetic use. When they are applied alone to the circumanal region, sticking feeling unfavorably remains. However, the combined use of a silicone oil in accordance with the invention results in loss of such sticky feeling and furthermore in synergistic addition of smoothness and refreshingness. The composition according to the invention is thus very favorable from the practical standpoint.

The silicone oil to be used in accordance with the invention is preferably a straight-chain dimethylsilicone or cyclic dimethylsilicone having a viscosity of not more than 30 cs as measured at 5° C.

The oils to be used in accordance with the invention may be used either alone or in combination of two or more. The silicone oil is preferably incorporated in an amount such that the whole composition may have a viscosity of not more than 30 cs as measured at 5° C. Thus, it is preferably added in an amount of 10 to 80% by weight (hereinafter, simply in %) based on the whole composition.

The cleansing and wiping composition according to the invention may, as desired, contain a microbicide, a pharmacologically active agent (e.g. antiinflammatory agent), an aroma chemical, and so forth, in addition to the above essential components.

For putting it to practical use, the cleansing and wiping composition according to the invention is filled in an appropriate container. It is especially convenient to use the composition in a sprayable form using either a propellant gas or a pressure-accumulating pump bottle.

The cleansing and wiping composition according to the invention is used, for example, in the following manner. Thus, after post-defecation wiping in the conventional manner with toilet paper or the like or on the occasion of diaper exchange, finish wiping is carried out with toilet paper or tissue paper sprayed several times with the composition according to the invention. The effects of this method of use can be further improved by wiping the circumanal region with tissue paper or toilet paper sprayed several times with the composition according to the invention after bathing or prior to defecation. In another mode of use, the composition according to the invention is directly applied to the cicumanal region, followed by wiping off with toilet paper or tissue paper, for instance.

Further, the composition according to the invention can be prepared or used in the form of an impregnated material. As a support material for impregnation, may for example be mentioned paper, nonwoven fabric, cloth, polymer film, sponge and foamed plastics, among which, paper and nonwoven fabric are especially preferred.

When the composition to be impregnated has large impregnation coefficient, the impregnation may be carried out either firstly immersing the support material into above-mentioned oils, followed by removing the excess oil by a pressurizing means etc., or directly spraying the oils to the support material. On the other hand, when the composition has small impregnation coefficient, similar procedures can be carried out but using mentioned oils admixed with organic solvents such as n-hexan, followed by removal of the solvents. The impregnation method, however, is not limited to the above.

A preferred manner of use of the cleansing and wiping composition thus prepared is, for example, a finish wiping after post-defacation wiping in the conventional manner with toilet paper etc., or on the occasion of diaper exchange. The effects of the cleansing and wiping material can be further improved by wiping the circumanal region with the cleansing material according to the invention after bathing or prior to defecation.

The following examples illustrate the invention in more detail.

EXAMPLE 1

After defecation, two panelists wiped the circumanal region in the conventional manner with toilet paper. When the coloration of toilet paper by excrement residue was no more observed by the naked eye, they further wiped said region with toilet paper sprayed with a composition according to the invention (mixture of 40% squalane, 40% glycerol tri-2-ethylhexanoate and 20% silicone) or with cleansing cotton (commercially available product). The amount of excrement residue wiped off by the latter treatment was determined by assaying urobilin in excrement by the fluorescence method. The results thus obtained are summarized in Table 1.

TABLE 1

| | (in mg) | | | |
|---|---|---|---|---|
| | Composition according to the invention | | Commercial cleansing cotton | |
| Wiping | Panelist 1 | Panelist 2 | Panelist 1 | Panelist 2 |
| 1st | 0.105 | 0.158 | 0.155 | 0.219 |
| 2nd | 0.084 | 0.067 | 0.058 | 0.117 |
| 3rd | 0.081 | 0.042 | 0.041 | 0.086 |
| 4th | 0.055 | 0.037 | 0.030 | 0.071 |

Although definite comparison was impossible due to great individual differences, there was deemingly little difference with respect to the wiping effect. Thus, the composition according to the invention is comparable in wiping effect to cleansing cotton. While cleansing cotton has drawbacks, such as cold feeling and undisposability in a flush toilet, any of such drawbacks was not found at all with the composition according to the invention.

EXAMPLE 2

Human fresh feces (0.5 mg) were applied to the skin on the inner side of human forearm (about 1 $cm^2$ in area) and completely dried with a drier. Then, the feces were wiped off with toilet paper sprayed with a composition according to the invention (mixture of 40% squalane, 40% glycerol tri-2-ethylhexanoate and 20% silicone oil), toilet paper sprayed with water, or untreated toilet paper (control), under application of a wiping force of about 100 $g/cm^2$, and the wiping effect was evaluated.

The change in residual amount of feces with the number of wipings is shown in FIG. 1. From the figure, it can be seen that better wiping was attained in the case where the composition according to the invention or water was sprayed as compared with the control. Whereas there was little difference in the wiping effect between the composition according to the invention and water, the toilet paper, when sprayed with water, became easily breakable and difficult to use. The residual amount of feces was determined in the same manner as in Example 1.

EXAMPLE 3

After defecation, two panelists wiped the circumanal region in the conventional manner with toilet paper. When the coloration of toilet paper by excrement was no more observed by the naked eye, they further wiped said region with toilet paper sprayed with a composition according to the invention (mixture of 40% squalane, 40% glycerol tri-2-ethylhexanoate and 20% silicone oil). The amount of excrement wiped off additionally was determined in the same manner as in Example 1 for the case where the circumanal region had been wiped in advance with toilet paper sprayed with the composition according to the invention and for the case where no such wiping had been performed. The results thus obtained are shown in Table 2.

TABLE 2

| | (in mg) | | | |
|---|---|---|---|---|
| | With prior use | | Without prior use | |
| Wiping | Panelist 1 | Panelist 2 | Panelist 1 | Panelist 2 |
| 1st | 0.239 | 0.085 | 0.491 | 0.501 |
| 2nd | 0.094 | 0.085 | 0.416 | 0.367 |
| 3rd | 0.040 | 0.074 | 0.260 | 0.370 |

TABLE 2-continued

| | (in mg) | | | |
|---|---|---|---|---|
| | With prior use | | Without prior use | |
| Wiping | Panelist 1 | Panelist 2 | Panelist 1 | Panelist 2 |
| 4th | 0.024 | 0.018 | 0.285 | 0.231 |

As is evident from Table 2, the residual amount of excrement in the circumanal region was smaller in the case where the composition according to the invention had been used in advance prior to defecation.

EXAMPLE 4

Figure 2:
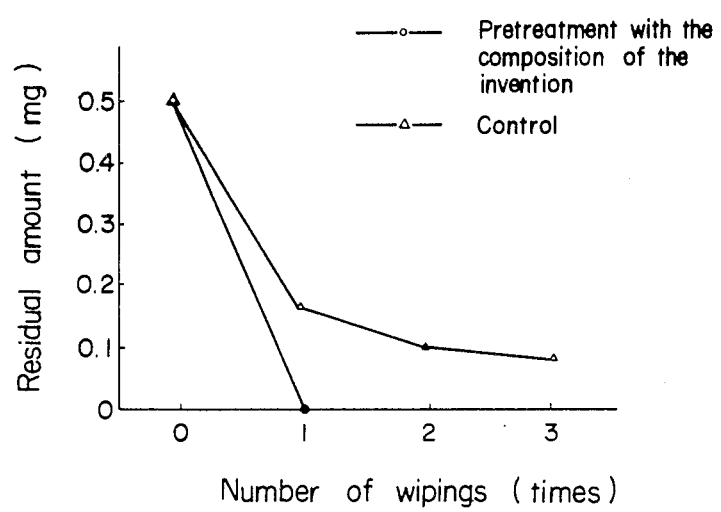
FIG. 2 is a graphic representation of the change in residual feces amount on the skin on the inner side of forearm with the number of wipings.

Following preliminary one wiping of the skin on the inner side of human forearm with toilet paper sprayed with a composition according to the invention (mixture of 40% squalane, 40% glycerol tri-2-ethylhexanoate and 20% silicone oil), 0.5 mg of fresh human feces was applied to said skin (about 1 cm$^2$ in area), followed by complete drying with a drier. Then, the feces were wiped off with toilet paper sprayed with the composition according to the invention, under application of a force of about 100 g/cm$^2$ and the cleansing effect was evaluated. In a control run, the above procedure was followed except that the preliminary wiping of the inner side of forearm with toilet paper sprayed with the composition according to the invention was omitted and that the wiping was performed with untreated toilet paper. The residual feces determination was conducted in the same manner as in Example 1. The results thus obtained are shown in FIG. 2.

What is claimed is:

1. A composition for cleansing and wiping the circumanal region consisting essentially of (1) at least one oil selected from the group consisting of vegetable oils, animal oils and synthetic oils and (2) 10 to 80 wt. % of a silicone oil, said composition having a viscosity of not more than 30 cs as measured at 5° C.

2. A composition for cleansing and wiping the circumanal region as set forth in claim 1, wherein said silicone oil is a straight-chain dimethylsilicone or cyclic dimethylsilicone having a viscosity of not more than 30 cs as measured at 5° C.

3. A composition for cleansing and wiping the circumanal region as set forth in claim 1, wherein said oil is jojoba oil, squalane or glycerol tri-2-ethylhexanoate.

4. A product for cleansing and wiping skin, consisting essentially of a solid support selected from the group consisting of paper, nonwoven fabric, cloth, polymer film, sponge and foamed plastics, wherein said support is impregnated with (1) at least one oil selected from the group consisting of vegetable oils, animal oils and synthetic oils and (2) 10 to 80 wt % of a silicone oil, said composition having a viscosity of not more than 30 cs as measured at 5° C.

5. The product of claim 4, wherein said solid suport is paper or nonwoven fabric.

6. The product of claim 4, wherein said solid support is toilet paper.

* * * * *